United States Patent [19]

Ginoux et al.

[11] Patent Number: 5,747,043
[45] Date of Patent: May 5, 1998

[54] *CUCUMIS MELO* PROTEIN EXTRACT WITH ANTIOXIDANT ACTIVITY AND PROCESS FOR PREPARING IT, COSMETIC COMPOSITION OR FOOD COMPOSITION CONTAINING SUCH AN EXTRACT

[75] Inventors: Jean-Paul Ginoux, Eyragues; Alain Dreyer, Chateauneuf de Gadagne; Philippe Roch, Eyragues; Jean-Claude Baccou, Montpellier; Dominique Lacan, St Beauzilles de Putois, all of France

[73] Assignee: Bio-Obtention SC, Montferrier-Sur-Lez, France

[21] Appl. No.: 775,802

[22] Filed: Dec. 31, 1996

Related U.S. Application Data

[63] Continuation of Ser. No. 398,940, Mar. 3, 1995, Pat. No. 5,616,323.

[30] Foreign Application Priority Data

Mar. 3, 1994 [FR] France .................. 94 02459

[51] Int. Cl.$^6$ .................. A61K 35/74; C12N 5/00
[52] U.S. Cl. .................. 424/195.1; 435/189; 424/94.2; 424/94.4; 514/844
[58] Field of Search .................. 424/195.1, 94.2, 424/94.4; 435/189, 240.1; 514/844

[56] References Cited

U.S. PATENT DOCUMENTS 5,180,676  1/1993  Ichikawa et al. .................. 435/240.1
5,616,323  4/1997  Ginoux .................. 424/195.1

FOREIGN PATENT DOCUMENTS 1404428  5/1965  France .
1-093 508  4/1989  Japan .

*Primary Examiner*—Shelley A. Dodson
*Attorney, Agent, or Firm*—Jacobson, Price, Holman & Stern, PLLC

[57] ABSTRACT

The subject of the present invention is a soluble *Cucumis melo* protein extract having a superoxide dismutase enzyme activity greater than 30 units/mg of proteins as well as, preferably, a catalase enzyme activity greater than 45 units/mg of proteins.

Preferably, the protein extract according to the invention is obtained from a *Cucumis melo* variety obtained by genetic crossing which has a shelf life of the order of 14 days such as the 95LS444 line or one of the hybrids obtained from this line.

The subject of the invention is also the use for cosmetic purposes (skin ageing, hair care), medical purposes (anti-cancer agents for the digestive system, antioxidant), food purposes (replacement of synthetic antioxidants) and contains, as active ingredient, an optionally purified protein extract.

12 Claims, No Drawings

CUCUMIS MELO PROTEIN EXTRACT WITH ANTIOXIDANT ACTIVITY AND PROCESS FOR PREPARING IT, COSMETIC COMPOSITION OR FOOD COMPOSITION CONTAINING SUCH AN EXTRACT

The present application is a continuation of application Ser. No. 08/398,940, filed Mar. 3, 1995, issued as U.S. Pat. No. 5,616,323 on Apr. 1, 1997.

The subject of the present invention is a *Cucumis melo* protein extract having an enhanced superoxide dismutase and possibly catalase enzyme activity and a process for preparing the said protein extract.

Its subject is also a pharmaceutical composition which can be used in the treatment of cancers or a pharmaceutical or cosmetic composition for external topical use, especially against skin ageing, containing such an extract. Its subject is also a food composition containing such an extract.

It has been known for a long time that atmospheric oxygen is one of the agents responsible for the deterioration of organic matter exposed to air. For this reason, the search for antioxidant substances has been the subject of a constant interest both in the field of cosmetology, food or medicine.

Patent FR-B-2,287,899 has described for example the application, in cosmetology, of superoxide dismutase enzymes and in particular the use of these enzymes in the preparation of cosmetic compositions for skin and hair care.

Superoxide dismutases are enzymes capable of inducing the dismutation of superoxide ions according to the reaction:

$$2O_2^- + 2H^+ \rightarrow H_2O_2 + O_2$$

These superoxide dismutases are especially extracted from bovine erythrocytes (Markovitz, J. Biol. Chem. 234, p. 40, 1959), from *Escherichia coli* (Keele and Fridovitch, J. Biol., 245, p. 6176, 1970) and from marine bacteria strains (Patents FR 2,225,443 and 2,240,277).

However, for reasons linked especially to the infectious substances which these materials may contain, there is currently a tendency to replace the latter by substances obtained from the plant kingdom which are reputed to be more healthy. These antioxidant enzymes are indeed present in variable quantities in some plants. It is also known that superoxide dismutases are capable of having anticancer actions in the digestive system by trapping the free radicals $O_2^-$ (communication by Professor Crastes de Paulet of the Faculty of Medicine and of INSERM of Montpellier).

The action of catalases on the hydrogen peroxide resulting from the action of superoxide dismutases reportedly permits the effects of the latter to be considerably increased by removing the hydrogen peroxide produced.

Nowadays, synthetic antioxidants for the preservation of foods are commonly used. The two principal synthetic antioxidants used are butylated hydroxytoluene (BHT) or butylated hydroxyanisole (BHA). However, it has recently been shown that these synthetic molecules could be toxic, in particular carcinogenic, and therefore dangerous at certain doses, hence the search for antioxidant substances of plant origin to replace them. Hemeda et al, 1990, J. of Food Science 55, 1, 184 and Farag et al, 1989, JAOCS, 66, 6, p. 800) have proposed to replace these compounds with substances obtained from plants.

In the fruit sector, there has been noted in certain climacteric fruits such as melon (*Cucumis melo*) superoxide dismutase activities of the order of 22 to 24 enzyme units per mg of proteins and a catalase activity of the order of 35 to 40 enzyme units per mg of proteins. In the case of tomatoes, the superoxide dismutase activity is situated at around 10 enzyme activity units per mg of proteins.

Climacteric fruits differ from nonclimacteric fruits, especially by the mode of maturation. The maturation phase of the fruits corresponds to an oxidative phenomenon from which a destruction of the membrane systems and a slowing down of the metabolic activity are observed. Concretely, the so-called climacteric fruits release ethylene autocatalytically at the beginning of the maturation phase. In these fruits, ethylene appears to initiate, coordinate and accelerate the entire physiological processes of maturation.

In contrast, nonclimacteric fruits do not exhibit this autocatalytic ethylene crises at the beginning of their ripening phase and it is not possible to modify maturation by application of ethylene.

Nonclimacteric fruits are in particular citrus fruits, grapes and strawberries, and climacteric fruits are in particular apples, pears, tomatoes, melons and bananas.

Surprisingly, new protein extracts of *Cucumis melo* were found which had an improved superoxide dismutase and possibly catalase enzyme activity.

It was also found that the new extracts could be advantageously used in cosmetology, especially against skin ageing, in the form of an appropriate cosmetic composition.

Another object of the present invention is to propose a new pharmaceutical composition containing, as active ingredient, these new protein extracts which are useful especially in the treatment of certain cancers.

Another object of the present invention is to propose a food composition containing such protein extracts as antioxidants, replacing in particular synthetic antioxidant molecules BHT and BHA and the like.

For this reason, the invention relates firstly to a protein extract, characterized in that it is obtained from *Cucumis melo* and in that it has a superoxide dismutase enzyme activity greater than 30 enzyme units per mg of soluble proteins as well as, preferably, a catalase enzyme activity greater than 45 enzyme units per mg of soluble proteins.

Generally, the protein extracts according to the invention have an improved superoxide dismutase and possibly catalase activity compared with known protein extracts obtained from most melons. The extracts according to the invention result from a selection from a large number of melons.

Catalase activity unit (U) designates the number of millimole of $H_2O_2$ reduced per minute. In a known manner, 1 gram of fresh material of a melon provides about 10 mg of soluble proteins.

The superoxide dismutase activity is measured in a known manner in unit per mg of soluble proteins. It should be understood that in its most general form, the protein extract according to the invention is such that for 1 gram of fresh material, 10 mg of soluble proteins are recovered. Under the same conditions, a protein extract of an ordinary melon will lead to a much lower SOD and catalase activity (from two to four times or more according to the cases).

The extract may also therefore comprise other soluble *Cucumis melo* proteins depending on the extraction process used.

According to a preferred variant, the protein extract according to the invention has a superoxide dismutase enzyme activity greater than 50 enzyme units per mg and possibly a catalase enzyme activity greater than 60 enzyme units per mg, advantageously a super-oxide dismutase enzyme activity greater than 60 units per mg and possibly a catalase enzyme activity greater than 100 units per mg.

More preferably still, the SOD activity is greater than 80 units per mg and possibly the catalase activity greater than 100 units per mg or possibly 110 units per mg.

This extract therefore contains, surprisingly, one or more enzymes possessing a SOD activity and one or more enzymes possessing a catalase activity according to the values indicated above.

According to another preferred variant, the protein extract is obtained from a *Cucumis melo* exhibiting a stable ethylene production after the ethylene crisis, that is to say that the production of ethylene presents a plateau which may be several days old. In general, climacteric fruits such as *Cucumis melo* have the property, with respect to preservation, of passing very rapidly from the mature state to the overmature state following the appearance of the paroxysm of the ethylene crisis. As is well known, the ethylene crisis in *Cucumis melo* is very substantial and the fruit begins to become disorganized shortly afterwards and its market value decreases. In contrast, in the case of *Cucumis melo* which are capable of providing a protein extract according to the invention, the emission of ethylene presents a plateau which is stable preferably for at least 5 days after the ethylene crisis and still more advantageously for at least 7 days.

This type of *Cucumis melo* is in particular described in International Patent Application WO 92/02622 of which the proprietor is the applicant company.

According to this patent application, the *Cucumis melo* variety obtained by genetic crossing has a longer shelf life (of the order of 10 to 14 days or more) than that of traditional varieties which is of about 5 days.

A macroscopic study carried out on slices of *Cucumis melo* as described in WO 92/02622 shows that the tissue structures are not damaged by the maturation (neither glassiness nor liquefaction linked to the destruction of the cells and characteristic of senescent tissues in *Cucumis melo* are observed).

Without the applicant wishing to be tied to any scientific interpretation, it is possible to emit the hypothesis that the long shelf life of *Cucumis melo* as described in the above-mentioned international application could be linked to the presence of a large quantity of antioxidant substances.

Persons skilled in the art, in the light of this patent application, will easily have available *Cucumis melo* which are capable of producing a protein extract according to the invention.

In particular, starting with the *Cucumis melo* line 95LS444 whose seeds have been deposited in accordance with the Budapest Treaty in the NCIMB collection (National Collection of Industrial and Marine Bacteria—ABERDEEN AB2 IRY (Scotland—GB) 23 St. Machar Drive) on 19th Jul. 1990 under number 40310, it is possible to obtain, by hybridization, other *Cucumis melo* varieties, for example varieties of the Vauclusien, Clipper and Supporter type, having the same characteristics which make it possible to obtain the protein extracts according to the invention.

The subject of the invention is therefore also a soluble protein extract as can be obtained from a *Cucumis melo* having an ethylene production plateau after the ethylene crisis, advantageously for at least five days, preferably for at least seven days.

Preferably, the protein extract is as can be obtained from the 95LS444 cell line or from one of the hybrid lines derived from 95LS444.

These protein extracts are as can be obtained by any process in the art which makes it possible to recover the soluble substance.

Advantageously, these protein extracts are as can be obtained by grinding or pressing, in aqueous medium, a *Cucumis melo* as described above at a pH of about 7.5, followed by the recovery of the supernatant.

The subject of the invention is also a process for preparing *Cucumis melo* protein extracts as described above, characterized in that *Cucumis melo* exhibiting an ethylene production plateau after the ethylene paroxysm as described above are ground in aqueous medium at an appropriate pH and in that the supernatant is recovered especially by centrifugation or filtration for possible subsequent purification.

The pH for such a process is preferably 5 to 9, which makes it possible to remain within optimal physiological conditions (without denaturation of the SODs and catalases).

Preferably, this is a centrifugation which makes it possible to discharge the membranous debris.

These *Cucumis melo* are preferably those described in Patent Application WO 92/02622.

The subject of the present invention is also a pharmaceutical or cosmetic composition for external topical use, especially against skin ageing or for hair care, containing as active ingredient a *Cucumis melo* protein extract having a superoxide dismutase enzyme activity greater than 30 enzyme units per mg and advantageously a catalase enzyme activity greater than 45 enzyme units per mg.

The present invention also relates to a cosmetic or pharmaceutical composition containing the protein extracts of the preferred variants as defined above.

This cosmetic composition has, in addition to the protein extract, an inert vehicle as is well known in the art of cosmetology.

Preferably, the protein extract will be in sufficient quantity so that the cosmetic composition applied to the skin offers a positive effect against ageing or offers a positive effect on the hair.

In general, the quantity of protein extract is in a quantity such that the cosmetic composition comprises 0.01 to 5% by weight of superoxide dismutase, preferably 0.01 to 1%.

These compositions are in particular described in Patent FR-A-2,287,899 to which persons skilled in the art can refer, and are for example lotion-type solutions, milk-type emulsions of liquid or semiliquid consistency, which are obtained by dispersing a fatty phase in an aqueous phase or vice versa or cream or gel type suspensions or emulsions of soft consistency. These compositions are prepared according to the customary methods.

Among the inert vehicles customarily used in the above-mentioned skin formulations, there may be mentioned surfactants, colorants, perfumes, preservatives, emulsifiers, liquid vehicles such as water, fatty substances such as natural or synthetic oils intended to constitute the fatty phase of the milks or creams, carboxyvinyl or maleic anhydride type resins neutralized by tertiary amines and especially by amino alcohols such as triethanolamine.

The hair compositions according to the invention may be in the form of aqueous, alcoholic or aqueous-alcoholic solutions, or in the form of creams, gels, emulsions or alternatively in the form of aerosol sprays also containing a propelling agent under pressure. They consist, for example, of shampoos, hair setting lotions, treatment lotions, styling gels or creams, dyeing compositions and the like. These compositions may contain various adjuvants usually present in these hair compositions, for example perfumes, colourants, preservatives, sequestrants, thickeners and the like.

The subject of the invention is also a pharmaceutical composition useful in particular in the treatment of certain cancers of the digestive system containing, as active ingredient, a *Cucumis melo* protein extract as defined above, in combination with one or more inert vehicles adapted to this use.

These compositions can be administered in oral or parenteral form or by any other route compatible with the desired treatment.

The subject of the invention is also a food composition containing, as antioxidant, a *Cucumis melo* protein extract as defined above at an effective dose.

The invention is now illustrated by the following examples which are given as a guide without limiting in any manner the scope of the invention.

EXAMPLES 1 to 8

Preparation of extracts and measurement of the enzyme activities of *Cucumis melo* extracts according to the invention, at various stages of maturation 5 g of pulp of a hybrid *Cucumis melo* derived from the 95LS444 cell line (described in International Application WO 92/02622) are used at various stages of maturation which constitute the different Examples 1 to 8.

The ethylene production curve for this variety is indicated in the accompanying sole figure, from the first day of harvest and has already been described in the abovementioned international application by the applicant.

According to a general mode of preparation: 5 g of pulp are ground in a mortar at cold temperature. One volume of 50 mM phosphate buffer (pH: 7.5; 1 mM EDTA; 5% glycerol), equivalent to 3 times the plant mass, is added.

After homogenization, the suspension was centrifuged at 5000 g at 4° C. for 30 minutes. The supernatant is then recovered and filtered; this crude extract is used to determine the catalase and superoxide dismutase activities as well as the protein contents.

The catalase activity is measured by monitoring, at 230 nm and at 25° C., the disappearance of the $H_2O_2$ substrate. The superoxide dismutase activity was measured he aid of a 525 SOD assay kit provided by the company Bioxytech. This method gives results which are comparable to those obtained by the McCord and Fridovitch method (inhibition by SOD of the reduction of cytochrome C by xanthine-xanthine oxidase). The soluble proteins were measured according to the Bradford method (1976).

The results are assembled in Table I below.

TABLE I

| Examples | Days after harvest | SOD activity U/mg proteins | Catalase activity U/mg proteins |
|---|---|---|---|
| 1 | 1 | 126 | 119 |
| 2 | 2 | 95.4 | 125 |
| 3 | 3 | — | — |
| 4 | 5 | 79.4 | 129 |
| 5 | 6 | — | — |
| 6 | 8 | 70 | 132 |
| 7 | 11 | 63 | 130 |
| 8 | 15 | 40 | 160 |

Comparitive Examples 9 to 16

Preparation of the extracts and measurement of the enzyme activities of extracts of control *Cucumis melo* at various stages of maturation The same tests carried out on Charente type common melons at the same maturation phases as the hybrid *Cucumis melo* obtained from the 95LS444 line are repeated.

The results are also indicated in Table II below.

These results show that the catalase and superoxide dismutase activities are very high in the case of the protein extracts according to the invention.

TABLE II

| Examples | Days after harvest | SOD activity U/mg proteins | Catalase activity U/mg proteins |
|---|---|---|---|
| 9 | 1 | 22.5 | 36.7 |
| 10 | 2 | 22.1 | 38.7 |
| 11 | 3 | 22.7 | 34.5 |
| 12 | 5 | 24 | 35.6 |
| 13 | 6 | 22.1 | 36 |
| 14 | 8 | — | — |
| 15 | 11 | — | — |
| 16 | 15 | — | — |

We claim:

1. Soluble protein extract, obtained from *Cucumis melo* and having a superoxide dismutase enzyme activity greater than 30 U/mg of proteins.

2. Soluble protein extract according to claim 1, having a catalase enzyme activity greater than 45 U/mg of proteins.

3. Soluble protein extract according to claim 1, wherein the superoxide dismutase enzyme activity is greater than 50 U/mg and catalase enzyme activity is greater than 60 U/mg.

4. Soluble protein extract according to claim 1, wherein the superoxide dismutase enzyme activity greater than 60 U/mg and catalase enzyme activity greater is than 100 U/mg.

5. Soluble protein extract according to claim 1, obtained from a *Cucumis melo* having an ethylene production plateau after the ethylene crisis.

6. Soluble protein extract according to claim 5, wherein *Cucumis melo* has an ethylene production plateau after the ethylene crisis for at least five days.

7. Soluble protein extract according to claim 6, obtained by grinding or pressing, in aqueous medium of, a *Cucumis melo* at a pH of 5 to 9, and recovery of the supernatant.

8. Pharmaceutical or cosmetic composition for external topical use, containing as active ingredient an optionally purified protein extract according to claim 1 and an inert vehicle.

9. Composition according to claim 8, wherein the amount of protein extract is such that the composition comprises 0.01 to 5% by weight of superoxide dismutase.

10. A method for treatment or prevention of aging comprising topically applying to skin of a human an effective amount of a composition according to claim 8.

11. The soluble protein extract of claim 5 wherein the *Cucumis melo* has an ethylene production plateau after the ethylene crisis for at least seven days.

12. The composition of claim 9 wherein the amount of protein extract is such that the composition comprises 0.01 to 1.0% by weight of superoxide dismutase.

* * * * *